United States Patent [19]

Nexo et al.

[11] Patent Number: 4,818,882
[45] Date of Patent: Apr. 4, 1989

[54] PHOTOACOUSTIC GAS ANALYZER

[75] Inventors: Sten A. Nexo; Jörgen Christensen, both of Birkerod; Ib E. Jorgensen, Copenhagen, all of Denmark

[73] Assignee: Aktieselskabet Bruel & Kjaer, Denmark

[21] Appl. No.: 52,596

[22] Filed: May 20, 1987

[30] Foreign Application Priority Data

May 27, 1986 [DK] Denmark ............... 2477/86

[51] Int. Cl.⁴ ........................................... G01N 21/00
[52] U.S. Cl. .................................. 250/343; 356/432
[58] Field of Search ............ 250/343; 356/432 T, 356/440

[56] References Cited

U.S. PATENT DOCUMENTS

| 2,674,696 | 4/1954 | Smith et al. | 250/345 |
| 2,767,321 | 10/1956 | Woodhull | 250/343 |
| 2,844,729 | 7/1958 | Winterling et al. | 250/345 |
| 3,562,524 | 2/1971 | Moore et al. | 250/343 |
| 3,904,880 | 9/1975 | Benz et al. | 250/343 |
| 4,008,394 | 2/1977 | Risgin et al. | 250/345 |
| 4,019,056 | 4/1977 | Block et al. | 250/344 |
| 4,355,233 | 10/1982 | Warnke et al. | 250/343 |
| 4,657,397 | 4/1987 | Oehler et al. | 356/414 |
| 4,740,086 | 4/1988 | Oehler et al. | 356/432 T |

FOREIGN PATENT DOCUMENTS

| 967633 | 11/1957 | Fed. Rep. of Germany. | |
| 1098244 | 1/1961 | Fed. Rep. of Germany. | |
| 2827230 | 8/1983 | Fed. Rep. of Germany. | |
| 34581 | 3/1978 | Japan | 250/343 |
| 465560 | 6/1975 | U.S.S.R. | 250/343 |

OTHER PUBLICATIONS

Goldan et al., "An Acoustically Resonant System for Detection of Low-Level Infrared Absorption in Atmospheric Pollutants," *Journal of Applied Physics*, vol. 45, No. 10 (10/74).

"Air Pollution: Sensitive Detection of Ten Pollutant Gases by Carbon Monoxide and Carbon Dioxide Lasers," *Science* vol. 177, pp. 347-349, (Jul. 28, 1972).

*Primary Examiner*—Janice A. Howell
*Assistant Examiner*—Constantine Hannaher
*Attorney, Agent, or Firm*—Scully, Scott, Murphy & Presser

[57] ABSTRACT

A photoacoustic gas analyzer comprising a measuring chamber, a modulated light source, and at least one microphone in connection with the measuring chamber and measuring the changes of pressure caused by the absorption of the light in the chamber. The measuring chamber comprises an inner surface with a reflecting coating. The measuring signal is thereby proportional to the gas concentration and is not provided as the difference between two almost equal values. As a result it is possible to measure small gas concentrations provided the light intensity within the measuring chamber suffices.

9 Claims, 5 Drawing Sheets

CONCENTRATOR 50
MEASURING CHAMBER 52

OPTICALLY REFLECTING COATING 56

OPTICALLY TRANSPARENT MATERIAL 58
HAVING LOW ABSORPTION

MICROPHONE 15

FIG. 6

MICROPHONE 16

SAMPLE FILTER 60   REF. FILTER 62

PHOTOACOUSTIC GAS ANALYZER

FIELD OF THE INVENTION

The invention relates to a photoacoustic gas analyzer comprising a measuring chamber, a modulated light source, and at least one microphone connected with the measuring chamber and measuring the changes of pressure caused by the absorption of the light within the chamber.

The above measuring method utilizes the fact that molecules absorb light such as for instance infrared light at predetermined wave lengths. The position of the absorption bands depends on the substance. The infrared light is modulated and an acoustic signal is generated in the measuring chamber, said signal being proportional to the concentration and having a frequency corresponding to the modulation frequency.

BACKGROUND ART

A known method for measuring the gas concentration is the so-called transmission method, cf. U.S. Pat. No. 3,562,524. This method is based on a measurement of how much the light is alternated at the passage of a gas cell, the difference in light intensity measured with and without the desired gas in the cell indicating the gas concentration. The reliability of the measurement is consequently rather low at low gas concentrations.

The above draw-back is avoided by the photoacoustic measuring method because the signal provided by this method is directly proportional to the gas concentration and not—as in the transmission method—proportional to the difference between two almost equal values. This method is therefore particularly suited for measuring low gas concentrations provided the light intensity within the measuring chamber is sufficiently high.

Figure 1:
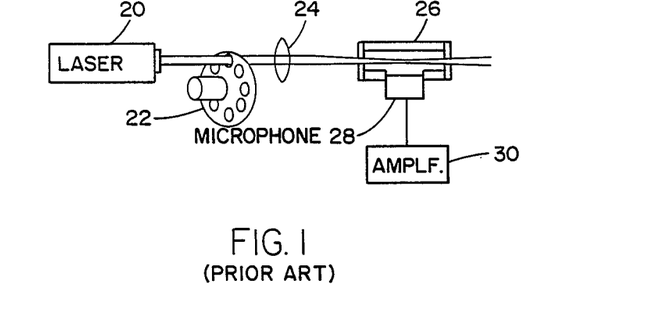
FIG. 1 illustrates a known photoacoustic measuring method employing a laser.

A known photoacoustic measuring method with a high sensitivity is based on the use of a laser as light source, cf. FIG. 1, the latter partly utilizing the great light power emitted e.g. by a carbon dioxide laser and partly the collimated nature of the light emitted. The light source of the laser is, however, not very flexible concerning a variation of the wave length. In addition, a high-energy laser such as a carbon dioxide laser is expensive, heavy, and large and therefore not suited for mass production.

The almost parallel light is a condition by the known photoacoustic measuring method and may, of course, derive from another type of light source such as a thermal light source or a spectral lamp instead of the light source of the laser. In this manner a high flexibility concerning the choice of wave length is obtained for instance by using an optical filter for the selection of the desired wave length interval. Such a light source is furthermore inexpensive, small, and easy and therefore suited for mass production. The intensity of an almost parallel light beam deriving from said sources is, however, very low as it is proportional to $\sin^2 \theta$, where $\theta$ is the angle of divergence of the light.

If a highly divergent light focussed on the measuring chamber is used a highly increased light intensity is instead obtained. The latter is, however, encumbered with the draw-back that an essential part of the light hits the walls of the measuring chamber and is thereby partially absorbed. As a consequence the measuring signal is partially reduced because only part of the light passes the measuring chamber, and furthermore a strong background signal is caused by the light power absorbed in the wall of the chamber.

SUMMARY OF THE INVENTION

An object of the present invention is to show how a photoacoustic transducer comprising for instance a thermal light source can provide a high sensitivity. The high sensitivity is obtained in two ways: Partly by maximizing the light intensity and consequently the signal level, and partly by minimizing disturbing signals.

The present invention provides a photoacoustic measuring chamber, the alls of which reflect the light hitting said walls from the inside. In this manner the light entering the measuring chamber passes said chamber and thereby contributes to providing the desired gas signal. Furthermore the disturbing background signal is minimized as only a small part of the light is absorbed by the walls of the chamber. The background signal can be further reduced by producing the walls of the chamber of a material of a high heat conductivity such as for instance copper with a thin layer of a reflecting coating such as gold.

The light intensity in the measuring chamber and consequently the sensitivity are increased by a factor 2 when one window of the measuring chamber is replaced by a reflecting wall, the light then passing the measuring chamber twice.

According to a more universal embodiment the measuring chamber comprises a hollow body of an arbitrary shape with walls of a highly heat-conducting material and with an inner reflecting coating. The light entering the measuring chamber is then reflected at the walls several times before leaving the chamber, whereby the intensity is amplified by a factor of up to 4. A spherical measuring chamber is an example of such a measuring chamber.

A further amplification of the intensity can be obtained by means of a concentrator allowing entry of light at an angle of incidence of $\theta < \theta_{max}$. The light is reflected therefrom and does not enter when $\theta > \theta_{max}$. The divergence of the light leaving the concentrator has then been increased, and the intensity is increased as well.

In order to obtain a sufficiently low wall background signal it is necessary that the reflecting coating absorbs only little of the light. The latter is relatively easily obtained by means of infrared light, but not by means of ultraviolet light. A measuring chamber particularly suited for the ultraviolet field is provided with walls of a transparent dielectric material of a low heat conductivity such as quartz and with the reflecting coating such as aluminium being applied onto the outside of the measuring chamber. In this manner the wall background signal is considerably reduced.

An infrared gas analyzer with two substantially uniform microphones connected to the measuring chamber allows a compensation for vibrations when the two uniform microphones are symmetrically situated relative to the centre of gravity of the air contained in the measuring chamber and the signals of the two microphones are added.

The microphones are shaped in a particular manner as the pressure-balancing channel from the back volume of each microphone usually extending to the surroundings here is connected to the volume of the closed measuring chamber. As a result, the disturbances due to acoustic noise from the outside are reduced.

When the transducer is provided with an additional optical filter, i.e. a reference filter, and a mechanical device switching between the two filters it is possible to compensate for the disturbing signals such as the wall background signal, the signal from a possibly interfering gas or the water continuum signal. The latter derives from a slight wide-band absorption in water steam, i.e. the so-called "water continuum absorption".

According to an alternative embodiment of the above reference filter compensation the modulator and the two filters are combined into a rotating unit. i.e. the so-called differential filter modulator. In this manner a separate mechanical filter-switching device is avoided, and furthermore the signal-to-noise value is increased by 6 dB.

The compensation of the water continuum signal can be provided by a photoacoustic measurement of the water concentration by means of an electrically modulated glow lamp as light source instead of using a particular reference filter. The method is based on the fact that the spectral distribution of the light from the glow lamp coincides with an absorption band positioned in the wave length interval 1.5–2.7$\mu$, said spectral distribution being determined by the spectral characteristics of the glow lamp and the transmission characteristics of the lamp glass. Such a method is very simple and inexpensive.

According to an embodiment magnetic valves are provided in the inlets of the measuring chamber. These magnetic valves close the measuring chamber during a measuring procedure, which ensures a further reduction of the acoustic noise. However, such a measuring procedure is discontinuous and the time of response is rather long. According to a second embodiment the magnetic valves are replaced by acoustic low-pass filters capable of strongly reducing acoustic noise from the outside at the modulator frequency. In this manner it is possible to measure continuously during the passage of gas, which ensures a short time of response. The sensitivity is, however, slightly reduced.

According to a particularly advantageous embodiment of the acoustic filters the acoustic capacity corresponds to the side volume not passed by the gas to be measured. In this manner the modulator frequency is highly reduced without sacrificing the short time of response.

A transducer with a plurality of optical filters as well as a mechanical device for a sequential coupling thereof makes is possible to perform a sequential measuring of the gas concentration in a mixture of several gases. A quick simultaneous parallel measuring of several gases can be obtained by the transducer being formed in such a manner that the light is distributed between a number of permanent optical filters and by the modulator being formed in such a manner that the light corresponding to said filters is modulated at their respective frequency. The signals corresponding to the various gases are separated through an electric filtration of the microphone signal.

If desired, the inrared gas analyzer can be combined with a paramagnetic measuring apparatus and employ the same measuring microphones. Then the paramagnetic gas analyzer can be used for measuring the oxygen content whereas the infrared gas analyzer can be used for measuring the content of the remaining gases.

BRIEF DESCRIPTION OF DRAWINGS

The invention will be described more detailed below with reference to the accompanying drawings, in which FIG. 8 illustrates a measuring chamber with magnetic valves or acoustic low-pass filters in the inlets, FIGS. 9a and 9b illustrate acoustic filters, while

DETAILED DESCRIPTION OF THE DRAWINGS

FIG. 1 illustrates a known prior art photoacoustic measuring system employing a laser 20, a modulator 22, a converging lens 24, a gas cell 26, a microphone 28, and an output amplifier 30.

Figure 2:
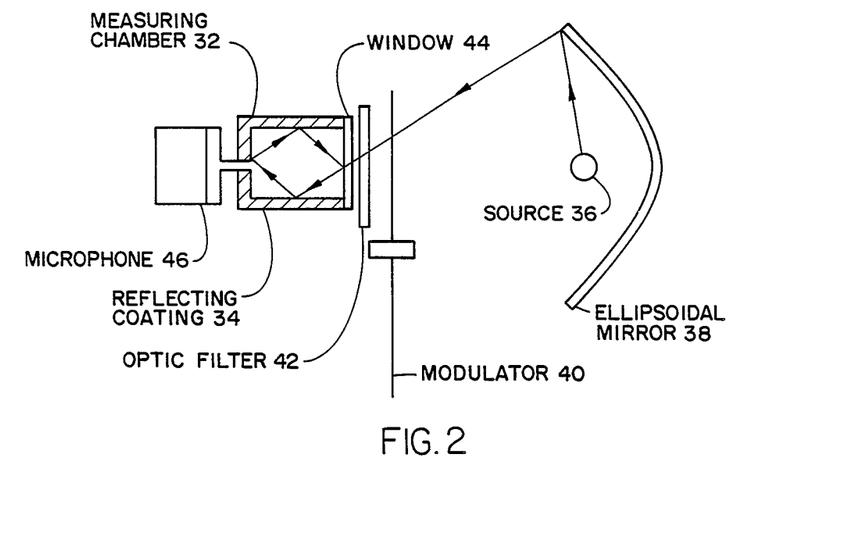
FIG. 2 illustrates a photoacoustic measuring chamber with reflecting walls allowing the use of a divergent light from a thermal light source.

FIG. 2 illustrates a photoacoustic measuring chamber 32 in the shape of a cylinder with a reflecting coating 34 on the interior walls, allowing the use of divergent light from a thermal light source 36. An ellipsoidal mirror 38 converges the light through a modulator 40, an optical filter 42, and an entrance window 44, from which the light diverges into the cylindrical chamber 32, with a microphone 46 providing the output therefrom.

Figure 10:
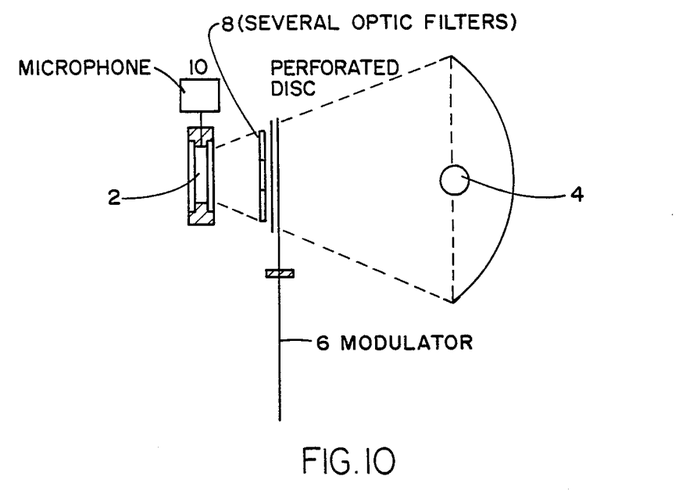
FIG. 10 illustrates a photoacoustic transducer for a simultaneous measurement of several gases of a mixture of gases.

The gas analyzer of FIG. 10 comprises a measuring chamber 2 and a light source 4. A modulator 6 and a filter 8 is placed between the measuring chamber 2 and the light source 4. The modulator 6 is a rotating disc with apertures, cf. FIG. 11. The modulator 6 causes emission of a pulsating light beam to the measuring chamber. The absorption within the measuring chamber 2 and the resulting heating of the gases contained therein imply that an acoustic signal is generated in the measuring chamber 2. This signal is detected by means of a microphone 10 communicating with the measuring chamber. The acoustic signal is proportional to the concentration of the gas to be analyzed and possesses a frequency corresponding to the frequency of the modulator.

Figure 11:
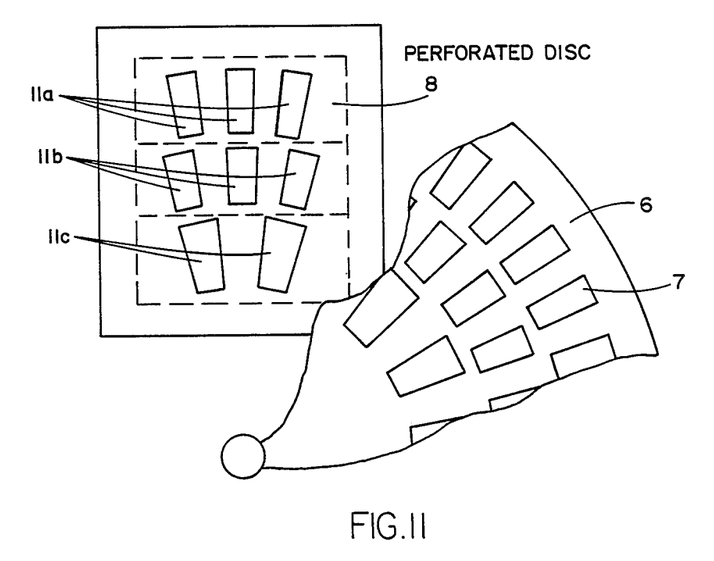
FIG. 11 is a front view of the modulator of FIG. 10.

FIG. 11 illustrates the modulator 6 in connection with some stationary filter openings 11a, 11b, 11c transmitting infrared light at the wave lengths abosrbed by $N_2O$, $CO_2$, and anaesthetics, respectively. The light is modulated simultaneously at three different frequencies. In this manner it is possible to measure the concentration of the three gases simultaneously.

The sound pressure of the photoacoustic signal is $$P = \frac{\sqrt{2}\,(\gamma - 1)}{\pi \omega} \times CKI$$

where
- I = the average light intensity within the measuring chamber
- C = the gas concentration
- K = the absorption coefficient,
- $\omega$ = the modulator frequency and
- $\gamma = C_P/C_v$, where $C_P$ is the amount of heat necessary for heating one mol of the gas by one degree at constant pressure (molar heatp $C_P$), and $C_v$ is the amount of heat necessary for heating one mol of the gas by one degree at constant volume (molar heat $C_v$).

The sensitivity is thus proportional to the light intensity I. Furthermore it is inversely proportional to the modulator frequency $\omega$. The formula applies, however, only to a predetermined lower limit frequency depending on the size of the chamber.

In order to increase the sensitivity it is thus desired to increase the light intensity.

Figure 12:
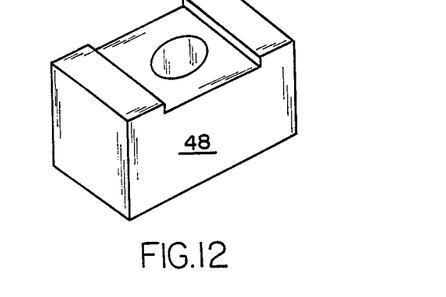
FIG. 12 is a perspective view of an example of a measuring chamber.

FIG. 12 is a perspective view of an exemplary embodiment 48 of a measuring chamber of the type described herein.

Figure 3:
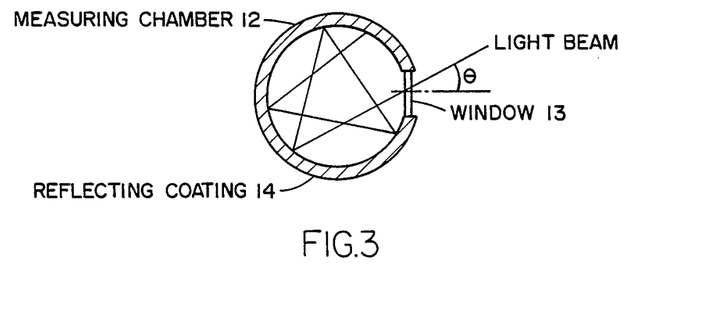
FIG. 3 illustrates an example of a second embodiment of the measuring chamber.

FIG. 3 illustrates a spherical measuring chamber 12 having an internal reflecting coating 14 and a relatively small window 13. The light of the source is focussed by means of a mirror. The light is heavily convergent which means that the entering light intensity is high. The inner surface of the spherical measuring chamber has been polished and coated with a material being highly reflecting in the desired wave length interval, e.g. gold or rhodium. The light entering the measuring chamber 12 is reflected several times before delivering from the chamber. In this manner the light intensity is amplified within the measuring chamber 12 compared to the entering light intensity. The maximum amplification is 4 times. The divergent entering light and the amplification through the multireflector ensure a high sensitivity. A condition of the method is a high reflection capacity, partly to maximize the amplification as much as possible and partly to reduce the background signal caused by part of the light being absorbed in the wall of the measuring chamber. The background signal can also be reduced by a suitable choice of wall material, tellurium copper and copper. Such a material must possess a high heat conductivity and a high heat capacity.

Figure 4:
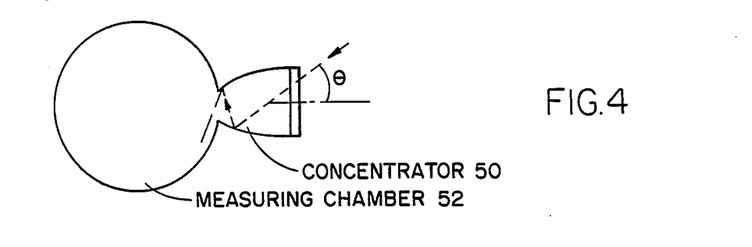
FIG. 4 illustrates the measuring chamber with a concentrator.

An additional amplification of the intensity can be obtained by means of a concentrator 50 situated at the opening of the measuring chamber 52, cf. FIG. 4. A concentrator is capable of allowing passage of light of an angle of divergence $\theta < \theta_{max}$. When $\theta > \theta_{max}$ the light is reflected outwards again. The divergence of the light leaving the concentrator and entering the measuring chamber is high. The intensity (maximum amplification = $1/\sin^2 \theta_{max}$) is high as well.

The light leaving the concentrator can be more divergent (up to $\pi/2$) than by means of a lense.

Figure 7:
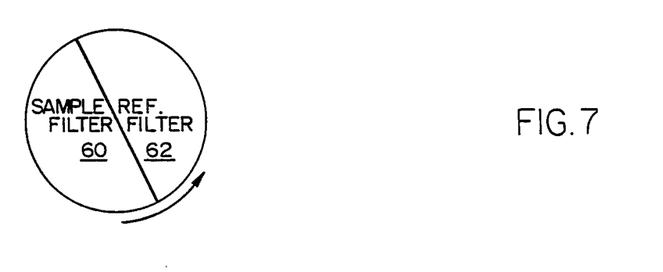

The differential filter modulator comprises two rotating optical filters, e.g. the configuration of FIG. 7 including two crescent-shaped filters, said filters being a sample filter 60 and a reference filter 62, respectively. The reference filter compensates for either the wall background, an interfering gas or a water continuum absorption.

Instead of the differential filter modulator it is possible to carry out the measuring sequentially by the first filter being switched on initially followed by a switching on of the second filter, said procedure being followed by an arithmetic compensation. The advantages of the filter modulator is that no filter-switching device is necessary and furthermore a 6 dB higher signal-to-noise-ratio is obtained during the same measuring period (3 dB because the dark period of the modulator is utilized for the measuring as well as 3 dB because the difference is measured directly).

Figure 5:
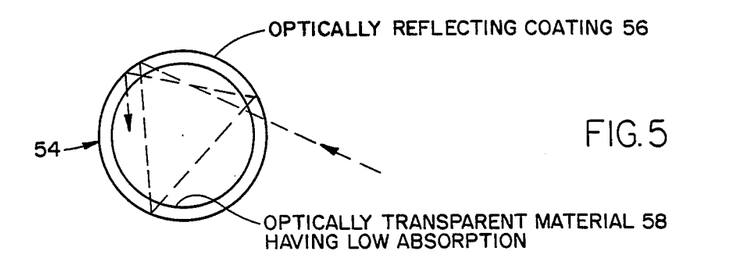
FIG. 5 illustrates a measuring chamber of transparent dielectric material with an outer reflecting coating.

According to a particularly preferred embodiment spherical measuring chamber 54 is provided with an outer reflecting coating, 56 cf. FIG. 5, whereby the wall background is reduced. The wall is made of a transparent material 58 and must be thermally thick, i.e. thicker than the thermal length of diffusion, said length of diffusion depending on the modulator frequency and the thermal properties of the material. A high heat conductivity means that the material possesses a long thermal length of diffusion, and then the wall must be extra thick.

According to an embodiment a cylindrical measuring chamber, 32 cf. FIG. 2, is included, said embodiment being particularly suited for mass production. Such a chamber is easy to polish. However, in return the amplification of the intensity is reduced by a factor 2 compared to the spherical embodiment, FIG. 12 is a perspective view of the measuring chamber, where it is possible to situate an optical filter in front of the measuring chamber. The measuring chamber is preferably situated in a block of tellurium copper, said material being easier to process than pure copper. The inner side of the measuring chamber is preferably coated with nickel and gold.

A compensation for the water continuum signal necessitates a measuring of the water concentration. The latter is carried out photoacousticly by means of the microphones and an electrically modulated glow lamp, the frequency characteristics of which correspond to $2.7\mu$ of the water band. In the latter case an arithmetic compensation based on the characteristics of each filter is carried out. The maximum cutoff frequency of the lamp glass is at $3\mu$ and thus not particularly influenced by the $CO_2$ band at $4.27\mu$. Therefore the optical filter can be omitted. An electrically modulated glow lamp allows omission of mechanical filter switches.

The water continuun absorption is a wide-band absorption in water steam. The absorption coefficient varies "softly" with the wave length. Generally speaking it is proportional to the water concentration square unlike the actual absorption bands having line structure and where the absorption is proportional to the concentration.

Figure 6:
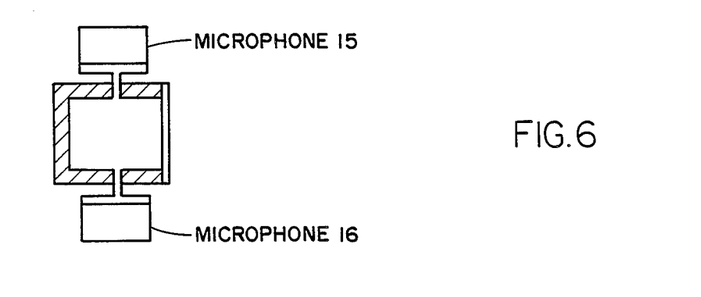
FIG. 6 illustrates a compensation for vibration by means of two microphones, FIG. 7 lillustrates an example of a differential filtering modulator.

The above embodiments are sensitive to vibrations. The vibration sensitivity is due partly to the mass of the membrane of the microphone, i.e. the membrane must consequently be thin, and partly to the mass of the air contained in the measuring. Two microphones 15, 16 are used for reducing the above sensitivity and are turned oppositely, cf. FIG. 6. Furthermore they are symmetrically positioned about the centre of gravity of the air contained in the measuring chamber. The signals of the two microphones 15, 16 are summed whereby the vibrations are avoided. Uniform microphones are necessary for a simultaneous compensation of the vibration signal from both the air and the membrane. Such an embodiment ensues an increase of the signal power by 6 dB as well as an increase of the signal-to-noise-ratio by 3 dB.

Each microphone may furthermore be shaped in such a manner that the pressure-balancing channel communicates with the measuring chamber and not with the surroundings in order to reduce the acoustic noise from the outside.

The size of the power cable of entering the measuring chamber by means of divergent light from a thermal light source can for instance by indicated by the fact that $9.8\mu$ and a band width of $0.7\mu$ result in about 13 mW.

Figures 8, 9A:
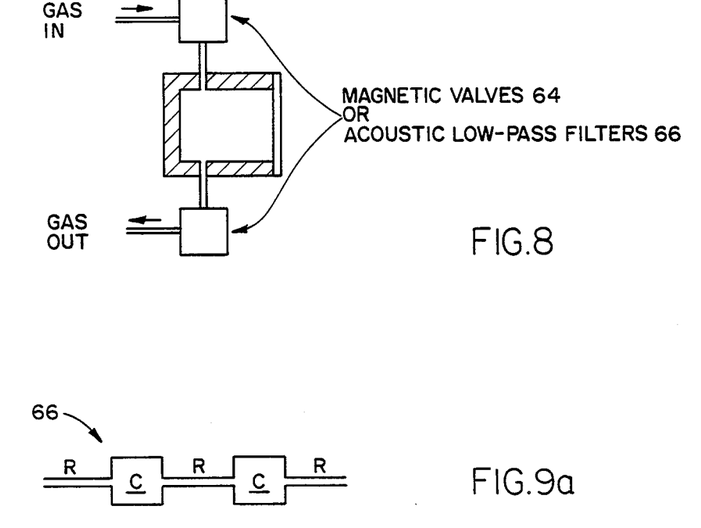

FIG. 8 illustrates a measuring chamber with magnetic valves 64 or acoustic low-pass filters 66 in the inlets. According to the embodiment of FIG. 8, magnetic valves 64 are provided in the inlets of the measuring chamber. These magnetic valves close the measuring chamber during a measuring procedure, which ensures a further reduction of the acoustic noise. However, such a measuring procedure is discontinuous and the time of response is rather long. According to a second embodiment, the magnetic valves are replaced by acoustic low-pass filters 66, FIGS. 9a and 9b, capable of strongly reducing acoustic noise from the outside at the modulator frequency. In this manner it is possible to measure continuously during the passage of the gas, which ensures a short time of response. The sensitivity is, however, slightly reduced. According to one particularly advantageous embodiment of the acoustic filters 64, the acoustic capacity corresponds to the side volume not passed by the gas to be measured. In this manner, the modulator frequency is highly reduced without sacrificing the short time of response.

A transducer with a plurality of optical filters as well as a mechanical device for sequential coupling thereof makes it possible to perform a sequential measurement of the gas concentration in a mixture of several gases. A quick simultaneous parallel measurement of several gases can be obtained by forming the transducer in such a manner that the light is distributed between a number of permanent optical filters and by the modulator being formed in such a manner that the light corresponding to the filters is modulated at their respective frequency. The signals corresponding to the various gases are separated through an electric filtration of the microphone signal, as illustrated by filtering circuit 68 of FIG. 9c.

If desired, the infrared gas analyzer can be combined with a paramagnetic measuring apparatus and employ the same measuring microphones. Then the paramagnetic gas analyzer can be used for measuring the oxygen content, whereas the infrared gas analyzer can be used for measuring the content of the remaining gases.

Figure 13:
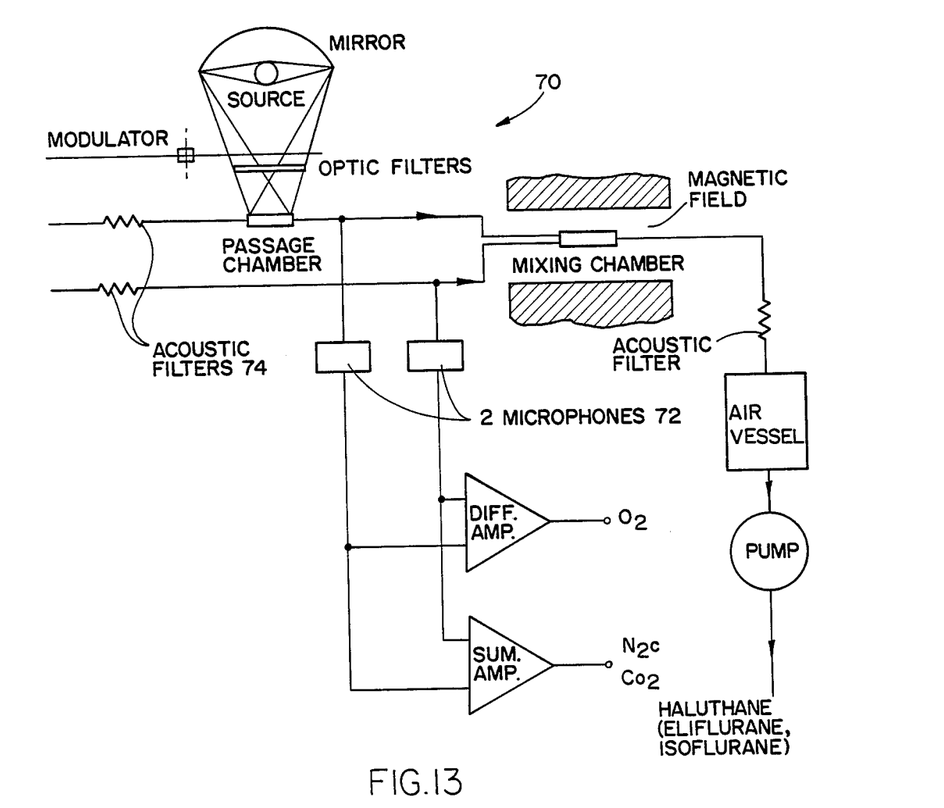
FIG. 13 illustrates a photoacoustic gas analyzer combined with a paramagnetic gas analyzer.

FIG. 13 illustrates a photoacoustic measuring apparatus 70 in connection with a paramagnetic measuring apparatus, the fact being utilized that the same microphones 72 can be employed in both cases. The photoacoustic measuring method is particularly suited for measuring for instance the $N_2O$ content whereas the paramagnetic measuring method is suited for measuring the oxygen content.

Figure 9B:
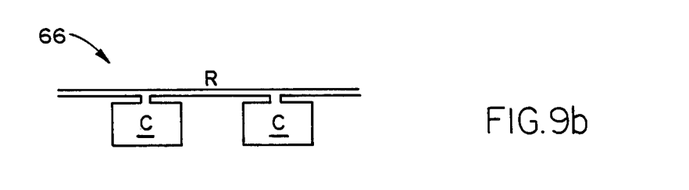
Figure 9C:
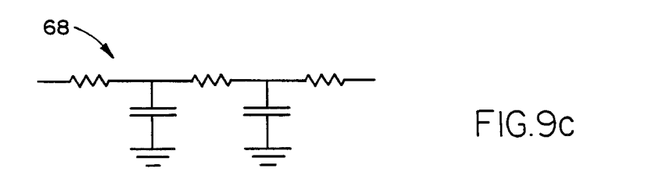
FIG. 9c illustrates an electric filtering circuit.

Each inlet of the measuring chamber is advantageously provided with acoustic filters excluding irrelevant acoustic signals, said acoustic filters being acoustic RC members. FIG. 9a illustrates a conventional RC member whereas FIG. 9b represents an acoustic RC member where C is represented by a side volume. A particular advantage of such a side volume is that a high acoustic lowering is obtained without the time of response being reduced. In this manner a quick measuring of several gases is allowed by a time constant of a few tenth of a second.

We claim:

1. A photoacoustic gas analyzer comprising a measuring chamber, a modulated light source directing light into the measuring chamber, and at least one microphone connected with the measuring chamber for measuring changes in pressure caused by the absorption of light by a gas within the measuring chamber, wherein substantially the entire measuring chamber comprises a curved wall and substantially the entire curved wall is reflecting, and is constructed from a heating absorbing material.

2. A photoacoustic gas analyzer as in claim 1, wherein the measuring chamber is constructed from a transparent material, and a reflecting coating is applied on the outer surface of the transparent measuring chamber.

3. A photoacoustic gas analyzer as in claim 1, further including an optical concentrator for providing divergent light into the measuring chamber.

4. A photoacoustic gas analyzer as claimed in 1, where two substantially uniform microphones are connected with the measuring chamber, wherein the two uniform microphones are symmetrically situated relative to the measuring chamber, and further including means for adding the output signals of the two microphones.

5. A photoacoustic gas analyzer as in claim 1, wherein the light directed into the measuring chamber is distributed between a plurality of optical filers, and further including a modulator which is shaped such that the light corresponding to the filters is modulated at their respective frequency.

6. A photoacoustic gas analyzer as in claim 5, wherein the modulator and the filters are combined in a rotating element.

7. A photoacoustic gas analyzer as in claim 1, wherein an acoustic filter which includes at least one acoustic RC member is positioned at the light input to the measuring chamber.

8. A photoacoustic gas analyzer as in claim 7, wherein said acoustic filter includes acoustic RC members with side chambers.

9. A photoacoustic gas analyzer as in claim 1, further including a compensation means for water continuum absorption, comprising a microphone and an electrically modulated glow lamp.

* * * * *

UNITED STATES PATENT AND TRADEMARK OFFICE
CERTIFICATE OF CORRECTION

PATENT NO. : 4,818,882         Page 1 of 2
DATED     : April 4, 1989
INVENTOR(S) : Sten Andersen Nexo, et al.

It is certified that error appears in the above-identified patent and that said Letters Patent is hereby corrected as shown below:

Figure 13: "$N_2c$ $C_o2$ HALUTHANE (ELIFLURANE, ISOFLURANE) "

should read as: -- $N_2O$ $CO_2$ HALOTHANE (ENIFLURANE, ISOFLURANE) --

Column 2, line 12: "alls" should read as --walls--

Column 5, line 15: "heatp" should read as --heat--

Column 6, line 50: "continuun" should read as --continuum--

UNITED STATES PATENT AND TRADEMARK OFFICE
CERTIFICATE OF CORRECTION

PATENT NO. : 4,818,882

DATED : April 4, 1989

INVENTOR(S) : Sten Andersen Nexo, et al.

It is certified that error appears in the above-identified patent and that said Letters Patent is hereby corrected as shown below:

Column 6, line 61: "measuring." should read as --measuring chamber.--

Column 8, line 42, Claim 5: "filers" should read as --filters--

Signed and Sealed this

Tenth Day of April, 1990

*Attest:*

HARRY F. MANBECK, JR.

*Attesting Officer*      *Commissioner of Patents and Trademarks*

UNITED STATES PATENT AND TRADEMARK OFFICE
CERTIFICATE OF CORRECTION

PATENT NO. : 4,818,882
DATED : April 4, 1989
INVENTOR(S) : Sten Andersen Nexo, et al.

It is certified that error appears in the above-identified patent and that said Letters Patent is hereby corrected as shown below:

Column 8, line 51: "input" should read as --inlet--

Signed and Sealed this

First Day of January, 1991

*Attest:*

HARRY F. MANBECK, JR.

*Attesting Officer*     *Commissioner of Patents and Trademarks*